United States Patent
Brumley et al.

[19]

[11] Patent Number: 5,868,030
[45] Date of Patent: Feb. 9, 1999

[54] CORE SAMPLE TEST METHOD AND APPARATUS

[75] Inventors: John L. Brumley, Duncan; David L. Meadows, Rush Springs; Billy J. Bennett, Duncan, all of Okla.

[73] Assignee: Halliburton Energy Services, Inc., Duncan, Okla.

[21] Appl. No.: 886,789

[22] Filed: Jul. 1, 1997

[51] Int. Cl.[6] ................................................ G01B 5/00
[52] U.S. Cl. ............................................................ 73/784
[58] Field of Search ........................... 73/794, 784, 789, 73/790, 818, 825, 38

[56] References Cited

U.S. PATENT DOCUMENTS

| | | | |
|---|---|---|---|
| 4,140,012 | 2/1979 | Hendricks | 73/861.27 |
| 4,495,795 | 1/1985 | Gupta | 73/38 |
| 4,599,891 | 7/1986 | Brauer et al. | 73/38 |
| 4,691,558 | 9/1987 | Vinson et al. | 73/64.1 |
| 4,868,751 | 9/1989 | Dogru et al. | 364/422 |
| 4,996,872 | 3/1991 | Mueller et al. | 73/38 |
| 5,050,493 | 9/1991 | Prizio et al. | 100/106 |
| 5,065,421 | 11/1991 | Morineau et al. | 378/208 |
| 5,226,310 | 7/1993 | Steiger | 73/38 |
| 5,228,347 | 7/1993 | Lowell et al. | 73/861.27 |
| 5,325,723 | 7/1994 | Meadows et al. | 73/794 |

FOREIGN PATENT DOCUMENTS

| | | |
|---|---|---|
| 794434 | 1/1977 | U.S.S.R. . |
| 1364708 | 1/1988 | U.S.S.R. . |
| 1716376 | 2/1992 | U.S.S.R. . |

OTHER PUBLICATIONS

Temco, Inc. catalog entry for a "Resistivity Core Holder, ECH Series" believed to be published prior to Sep., 1991.
Halliburton Services design of a temperature control cell disclosed or in use prior to Sep., 1991, labeled Exhibit 1.
Temco, Inc. catalog entry for an "Incremental Pressure Core Holder, DCH Series" believed to be published prior to Sep., 1991.

*Primary Examiner*—George M. Dombroske
*Assistant Examiner*—Jewel Thompson
*Attorney, Agent, or Firm*—Robert A. Kent; C. Clark Dougherty, Jr.

[57] ABSTRACT

A core sample test apparatus applies pressure to the core sample and measures responsive longitudinal deformation with two sensors and lateral deformation with two orthogonal pairs of diametrically disposed sensors. The apparatus holds the core sample under test in a sleeve to which no or insignificant end torsional forces are applied during installation due to rotationally blocked washers used adjacent the ends of the sleeve. Concurrent acoustic testing can also be applied.

19 Claims, 5 Drawing Sheets

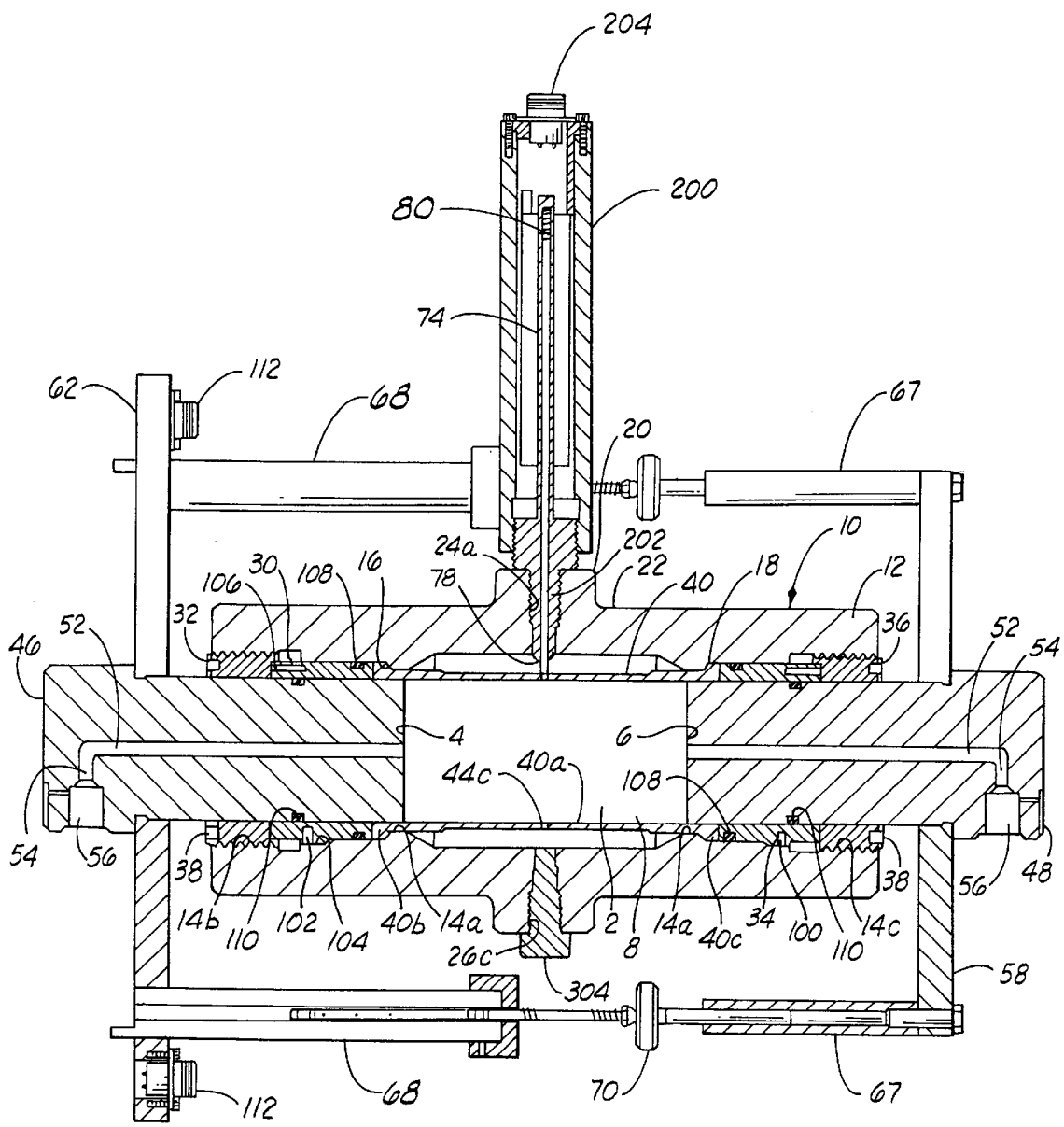

5,868,030

CORE SAMPLE TEST METHOD AND APPARATUS

BACKGROUND OF THE INVENTION

This invention relates generally to methods and apparatus for testing core samples extracted from an oil or gas well. In particular, the invention relates to a method of determining elastic properties of a core sample and an apparatus useful in performing the method, which apparatus is for detecting changes in longitudinal and lateral dimensions and/or acoustic properties of the core sample.

A commonly utilized technique for stimulating the production of hydrocarbons from a subterranean rock formation penetrated by a well bore is to create and extend fractures in the formation. Generally, the fractures are created by applying hydraulic pressure on the formation from the well bore. That is, a fracturing fluid is pumped through the well bore and into the formation at a rate and pressure such that the resultant hydraulic force exerted on the formation causes one or more fractures to be created. The fractures are extended by continued pumping; and the fractures can be propped open or flow channels can be etched in the faces of the fractures with acid, or both can be done, to provide openings in the formation through which hydrocarbons readily flow to the well bore. Fracturing is also utilized in carrying out enhanced production procedures in subterranean formations (e.g., water flooding from an injection well to a production well) as well as in other applications.

In designing fracturing treatments to be carried out in subterranean rock formations, it is often necessary and always desirable to know the direction in which fractures will extend in the formation. Such knowledge enables more efficient reservoir management. For example, knowing such directional information allows one to better place production wells for maximizing production from the reservoir of hydrocarbons in the subterranean formation and to better place waterflood injection wells for increasing waterflood sweep efficiency by avoiding an injection well arrangement that would cause premature breakthrough of the injected fluid into the producing well.

Information that can be used to help predict the size of the fracture includes Young's modulus and Poisson's ratio, which describe elastic properties of rock. These can be determined by testing rock core samples that have been extracted from an oil or gas well in a known manner.

Young's modulus can be defined as the ratio of normal stress to the resulting strain in the direction of the applied stress. Stress can be applied to a core sample with a longitudinal or axial compressive force from a known type of press. The resulting longitudinal or axial strain is the yield or deflection measurable as the change in the longitudinal or axial dimension of the core sample.

Poisson's ratio can be defined as the ratio of lateral or radial strain to the longitudinal or axial strain for normal stress within the elastic limit. This is measurable using the aforementioned detected dimensional change in conjunction with a lateral or radial dimensional change detected in response to the applied stress.

Prior proposals to obtain the foregoing information include the method and apparatus disclosed in U.S. Pat. No. 5,325,723 to Meadows et al., which is incorporated herein by reference. A modification of this apparatus has been built and used. This modified apparatus is shown in FIGS. 1–3 of the present specification. Features of the modified apparatus beyond what is described in the 5,325,723 patent include: two diametrically opposed sensors 500 (FIG. 2) for measuring longitudinal deflection, which sensors are connected to brackets attached to end caps of the apparatus; two sensors 502 (FIG. 3) in a uniform spatial pattern in a single plane around the circumference of the core sample 504 to measure lateral deflection; a pressure sealed container 506 for the moving components of each lateral displacement sensor, which container is capable of withstanding design pressure of the entire test apparatus thus eliminating friction on the measurement rods of the lateral displacement sensors; attachment of the lateral deflection sensors by the pressure sealed containers directly to the support body 508 of the housing containing the core sample; physical dimensions defined to accommodate testing softer formation materials; loading spacers 510 adjacent the end caps to allow application of hydraulic pressure to the end of the sample to obtain true hydrostatic stress load application on all surfaces when used with simpler loading frames; a port in one of the loading spacers to allow fluid flow through the sample for measurement of physical flow properties (permeability) as the stress applied to the sample is changed, thereby allowing a determination of the effect of stress loading on the sample; the length of annular washers 512 adjacent ends of the core sample sealing sleeve being made sufficient to allow the use of O-rings on the washers and end caps, and on any spacers adjacent the end caps, to seal the flow path through the core sample; and spring pressure applied at the back end of the radial measurement rod of each lateral deflection sensor 502, which spring pressure is applied completely within the pressurized environment to ensure that the pad surface is in contact, with the outside of the sealing membrane, thereby eliminating the problem of isolation between the core sample and the pressurizing fluid which can be caused by a leaking perforation required to place inserts through the flexible membrane as described in the 5,325,723 patent.

Despite the disclosure in U.S. Pat. No. 5,325,723 and the apparatus shown in FIGS. 1–3 of the present specification, there is still the need for an improved core sample test method and apparatus. Specifically, there is the need for greater understanding of directional variation of mechanical properties in underground formations. To achieve this, there is the need for the capability to monitor lateral deformation in two orthogonal directions. This will enable observation of directional anisotropy in the core sample specimen. In the absence of directional anisotropy, this will enable an improved accuracy to be obtained in the magnitude of lateral deformation through averaging the diametrical changes. There is also the need for ensuring that no torsion forces are induced upon the sample from the sealing sleeve so that proper sealing and measurements can be obtained. There is further need in the industry for greater understanding of the relationship between dynamically derived mechanical properties for underground formations and laboratory measured static mechanical property measurements. Incorporation of acoustic travel time measurement using an acoustic transmitter and an acoustic receiver will allow correlation of travel time with stress magnitude in the laboratory test cell. This will allow the development of correlations between static and dynamic mechanical property data.

SUMMARY OF THE INVENTION

The present invention satisfies the aforementioned needs by providing a novel and improved core sample test method and apparatus.

The present invention allows for the testing of multiple samples with a minimum of equipment disassembly and reassembly required between testing of samples. A sealing sleeve is used as in the prior art, but torsion forces in the sleeve are prevented by adding a key structure to washers which seal the sealing sleeve at its ends. The key structure prevents rotation of the washers that could otherwise occur due to mechanical friction between the washer and threaded holding or retaining members which apply sealing pressure to the washers. The incorporation of the non-rotatable washers reduces the instances of sealing sleeve distortion due to torsion loading of the sleeve material as the retaining members are tightened to ensure a pressure seal between the sealing sleeve and the body of the apparatus.

Four lateral measurement transducers provide more accuracy in determining the lateral displacement by providing measurement changes at four positions of the core sample being tested. The measurement in two perpendicular planes allows the identification of directional anisotropy in lateral deformation in the specimen. This enables more accurate analysis of the measurement data.

An acoustic measurement capability allows a determination of the impact of stress loading on the dynamically derived mechanical property values. Collection of sufficient data provides information in correlating the values currently provided by downhole acoustic logging measurement techniques with laboratory determined static mechanical property values.

The present invention provides an apparatus for testing a core sample extracted from an oil or gas well. In accordance with one definition of the present invention, this apparatus comprises: a housing having first and second ends; a sealing sleeve fixed inside the housing and adapted to receive a core sample without the sealing sleeve being removed from the housing; a first retainer, disposed within the first end of the housing; a second retainer, disposed within the second end of the housing; a first longitudinal deflection sensor connected to the first and second retainers; a second longitudinal deflection sensor connected to the first and second retainers; a first lateral deflection sensor; a first pressure sealed container connected to the housing, the first pressure sealed container having the first lateral deflection sensor disposed therein; a second lateral deflection sensor; a second pressure sealed container connected to the housing, the second pressure sealed container having the second lateral deflection sensor disposed therein; a third lateral deflection sensor; a third pressure sealed container connected to the housing, the third pressure sealed container having the third lateral deflection sensor disposed therein; a fourth lateral deflection sensor; and a fourth pressure sealed container connected to the housing, the fourth pressure sealed container having the fourth lateral deflection sensor disposed therein.

In accordance with another definition of the present invention, the apparatus comprises: a housing having first and second ends; a sealing sleeve fixed inside the housing and adapted to receive a core sample without the sealing sleeve being removed from the housing; a first retainer, disposed within the first end of the housing; a second retainer, disposed within the second end of the housing; longitudinal deflection sensing means for sensing a change in longitudinal dimension of the core sample in response to an applied force; and lateral deflection sensing means for sensing a change in lateral dimension of the core sample in response to the applied force. The housing of this apparatus includes: a support body having an inner surface providing support for the sealing sleeve inside the body; a first washer disposed within the support body adjacent an end of the sealing sleeve such that the first washer is not rotatable relative to the support body and the sealing sleeve fixed to the body; and a second washer disposed within the support body adjacent another end of the sealing sleeve such that the second washer is not rotatable relative to the support body and the sealing sleeve fixed to the body.

In accordance with a further definition of the present invention, the apparatus comprises: a housing having first and second ends; a sealing sleeve fixed inside the housing and adapted to receive a core sample without the sealing sleeve being removed from the housing; a first retainer, disposed within the first end of the housing; a second retainer, disposed within the second end of the housing; and the housing further having an acoustic signal generator access port and an acoustic signal receiver access port defined through the outside of the housing.

The present invention also provides all three of the foregoing in combination to provide in a single test apparatus both physical deflection (strain) measurements and acoustic measurements.

The present invention also provides a method of testing a core sample extracted from an oil or gas well, comprising steps of: (a) applying pressure to a core sample in a test vessel; (b) measuring a parameter of the core sample in the test vessel resulting from the applied pressure; and (c) concurrently with steps (a) and (b), performing an acoustic test on the core sample in the test vessel.

Therefore, from the foregoing, it is a general object of the present invention to provide a novel and improved core sample test method and apparatus. Other and further objects, features and advantages of the present invention will be readily apparent to those skilled in the art when the following description of the preferred embodiments is read in conjunction with the accompanying drawings.

BRIEF DESCRIPTION OF THE DRAWINGS

FIG. 5 is a sectional view of the core sample test apparatus of the present invention taken along line 5—5 in FIG. 4.

DETAILED DESCRIPTION OF THE INVENTION

Figure 4:
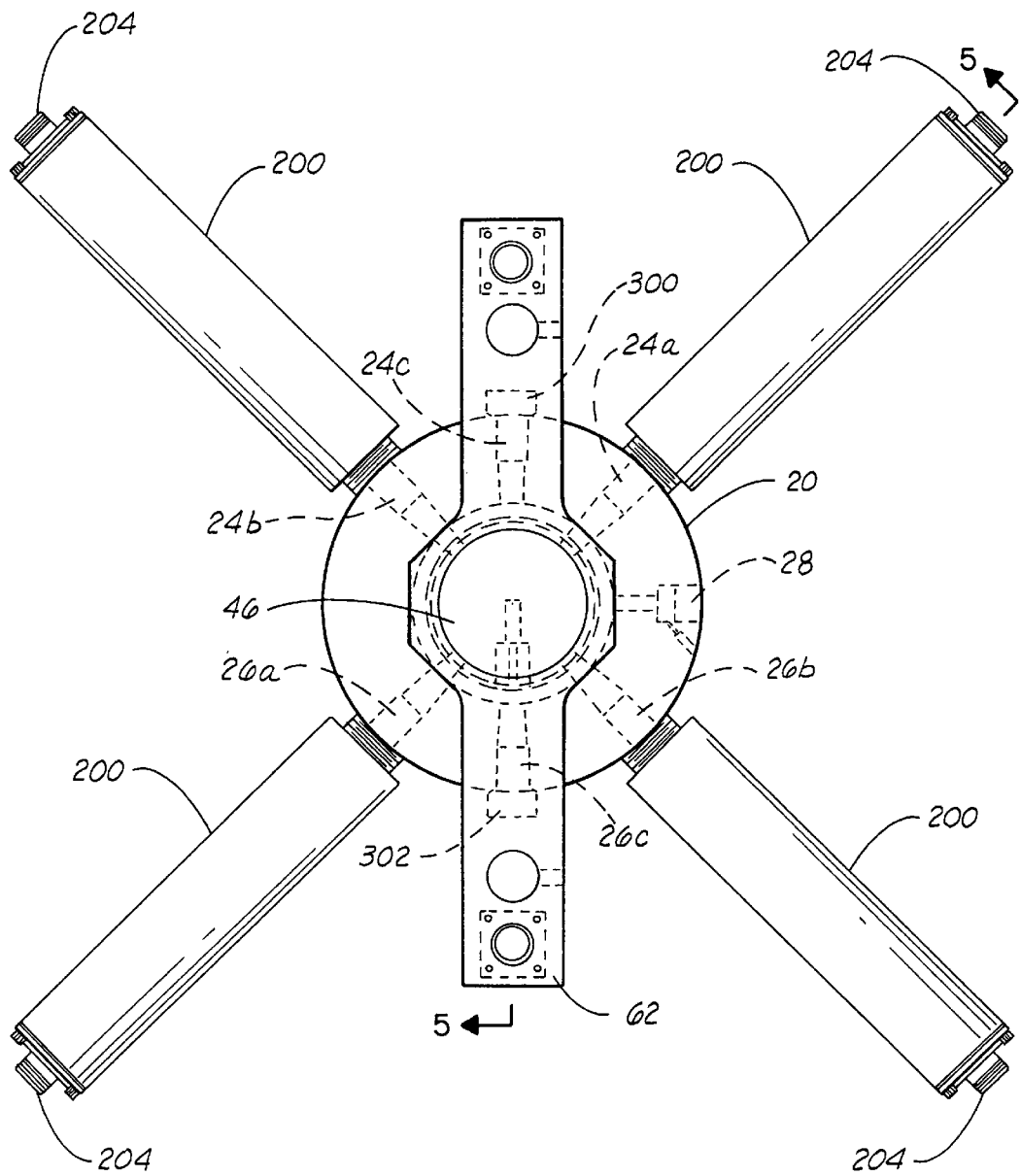
FIG. 4 is an end view of the preferred embodiment of the core sample test apparatus of the present invention.

Referring to FIGS. 4 and 5, the preferred embodiment of an apparatus for testing a core sample 2 extracted from an oil or gas well will be described. This apparatus can be used in performing the method of the present invention. It is preferably used in an upright orientation obtained by rotating clockwise or counterclockwise 90° from the orientation of FIG. 5.

The core sample 2 is typically cylindrical with two ends 4,6 and a side 8 extending between the ends 4, 6. It is extracted from an oil or gas well in a manner known in the art.

The apparatus of the present invention comprises a housing 10 defining a chamber in which the core sample 2 is tested. The housing 10 includes a unitary rigid support body 12 having a contoured cylindrical inner surface 14 providing support shoulders 16, 18. An axially central, radially innermost surface portion 14a is defined at a smaller diameter than radially outermost threaded surface portions 14b, 14c extending longitudinally from opposite ends of the central surface portion 14a. A circumferential flange 20 protrudes radially outwardly from a central portion of a cylindrical outer surface 22 of the support body 12. Three sets of two respective diametrically opposed openings 24, 26 are defined radially through the flange 20, and an opening 28 angularly offset from the openings 24, 26 is also defined through the flange 20.

Forming removable parts of the housing 10 are an annular washer 30, an exteriorly threaded annular holding member 32 connected to the threaded surface 14b of the support body 12 and adjacent the washer 30 to hold it in place, an annular washer 34, and an exteriorly threaded annular holding member 36 connected to the threaded surface 14c of the support body 12 and adjacent the washer 34 to hold it in place. The holding members 32, 36 have sockets 38 defined in their outer ends for receiving a spanner wrench to screw and unscrew the members 32, 36 relative to the support body 12; however, other constructions and configurations for inserting and removing the holding members can be used (e.g., engagement heads protruding from the main body, a T-shaped body, etc.). Furthermore, the washers 30, 34 can be of various designs. For example, each washer 30, 34 can have a curved side that engages the respective end of a sealing sleeve 40 to increase sealing pressure thereagainst when secured by the respective holding member 32, 36. The washers 30, 34 can also carry sealing members, such as a respective O-ring on the washer's inner circumference.

Each of the washers 30, 34 is preferably disposed within the support body adjacent a respective end of the sealing sleeve 40 such that the washers 30, 34 are not rotatable relative to the support body 12 and the sealing sleeve 40 fixed to the body. This prevents spinning or rotating of the washers and any resulting twisting of the sealing sleeve as the washers are pressed tightly against the sealing sleeve to ensure a competent pressure seal between the body and the sleeve. Twist or creases in the sealing sleeve can result in loss of pressure containment or error in measuring lateral displacement in the test fixture. More particularly, each of the washers 30, 34 has a radial notch or bore 100 into which a key 102, such as a pin or dowel, is inserted and retained. The key 102 is sufficiently long that it extends radially outwardly beyond the outer surface of the respective washer. This protruding portion of the key 102 is received within a channel 104 defined in the respective inner surface 14b, 14c of the support body. Thus, the channel 104 defines a keyway which allows the key 102 to slide longitudinally but not rotate circumferentially within the support body 12. To facilitate longitudinal sliding, each washer 30, 34 has a longitudinal bore 106 which can receive a screw or other elongated implement that is long enough to extend beyond the end of the support body 12 for being grasped by one inserting or extracting the respective washer.

Each washer 30, 34 also has an external circumferential groove that receives a respective O-ring 108 to seal against the inner surface of the support body 12.

The apparatus of the present invention further comprises the aforementioned sealing sleeve 40, which is supported inside the housing 10 and adapted to receive the core sample 2 without the sealing sleeve 40 being removed from the housing 10. The sleeve is made of a resilient material of a type known in the art, and is preferably what is referred to as a Hassler sleeve.

The illustrated sealing sleeve 40 has a cylindrical main body portion 40a with radially outwardly flaring ends 40b, 40c (however, to facilitate sliding the sleeve 40 into or out of the support body 12 upon assembling or reassembling the apparatus, one end such as end 40c can have a straight configuration). These illustrated ends 40b,40c are adjacent the shoulders 16, 18, respectively, of the support body 12, and the main body portion 40a of the sealing member is adjacent the surface 14a of the support body 12. This relationship properly locates the sleeve 40 relative to the support body 12 during assembly. This positioning also remains fixed by means of the washer/holding member pairs 30, 32 and 34, 36 disposed adjacent respective ends of the sealing sleeve 40. Three sets of two respective diametrically opposed openings 42, 44 are defined in the sleeve 40 and aligned with respective openings 24, 26 of the support body 12.

The apparatus also comprises retaining means for releasably retaining the core sample 2 within the sealing sleeve 40 and for transferring a longitudinal force to the core sample 2. The retaining means of the preferred embodiment includes two end caps 46, 48 slidably received in the housing 10 (specifically, within the washer/holding member pairs 30, 32 and 34, 36, respectively). Each end cap 46, 48 has an axial channel 52 and an intersecting radial channel 54. Each channel 52 opens through the end of the respective end cap that is adjacent a respective end of the core sample 2 when the apparatus is assembled as illustrated. Each channel 54 opens through the side of its respective end cap via a respective port 56. Each of the end caps 46, 48 has a smaller diameter cylindrical portion that is received into the housing and a larger diameter cylindrical portion that is outside the housing as shown in the drawings. The sides of the smaller diameter portions are preferably smooth so that the end caps can be easily pushed in and pulled from the housing 10 when there is no test pressure being applied. This smaller diameter portion of each end cap has a circumferential groove that receives a respective O-ring 110 to seal against the inner cylindrical surface of the respective washer 30, 34.

Figure 1:
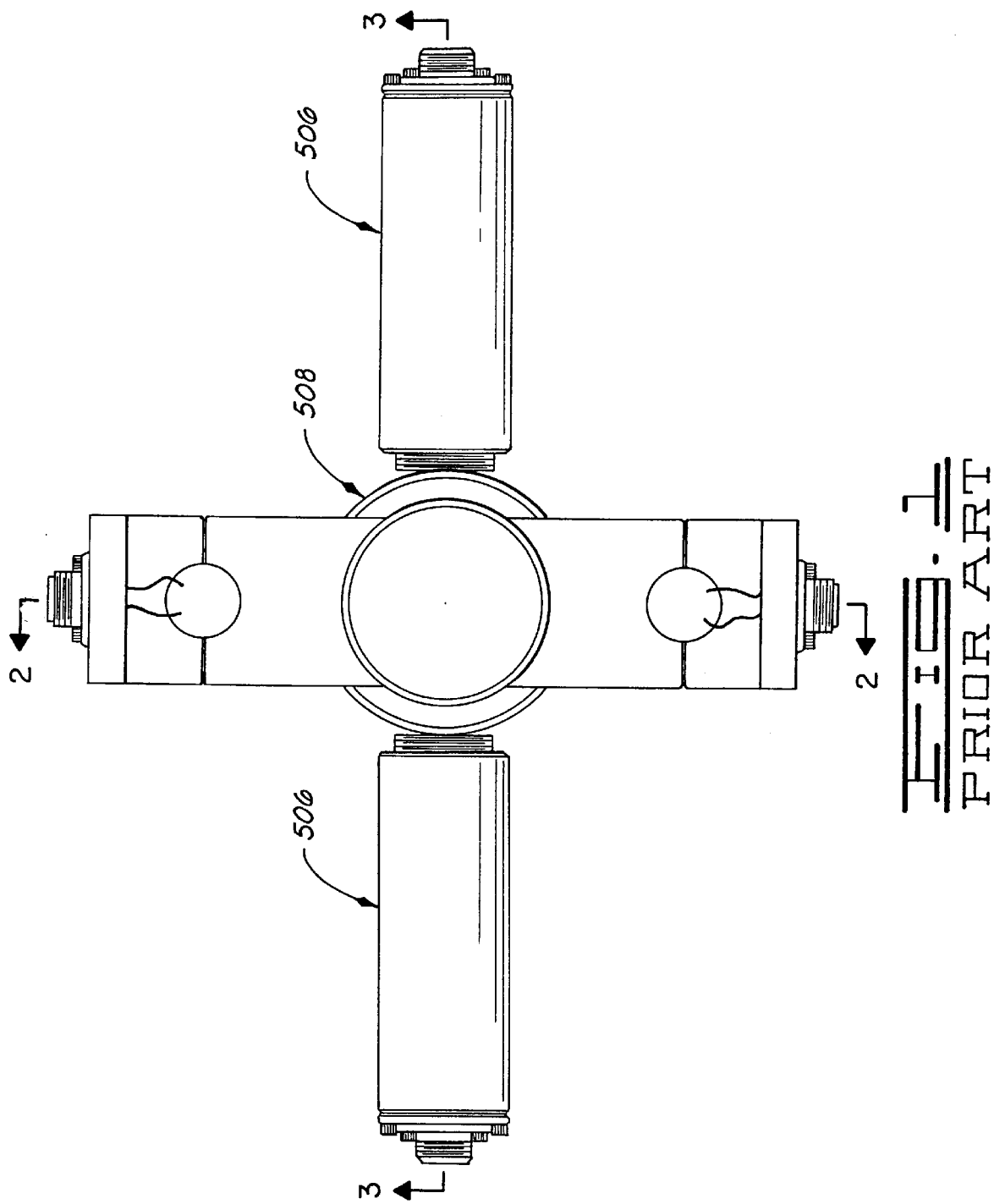
FIG. 1 is an end view of a prior art core sample test apparatus.
Figure 2:
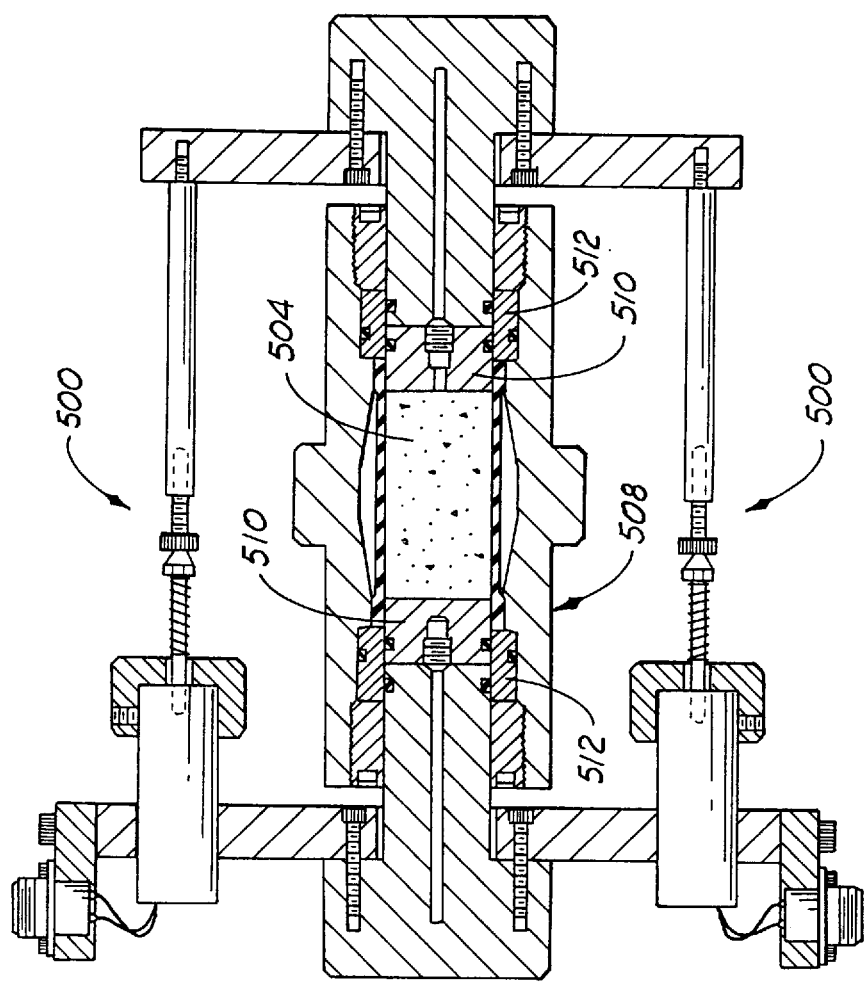
FIG. 2 is a sectional view of the prior art core sample test apparatus taken along line 2—2 in FIG. 1.
Figure 3:
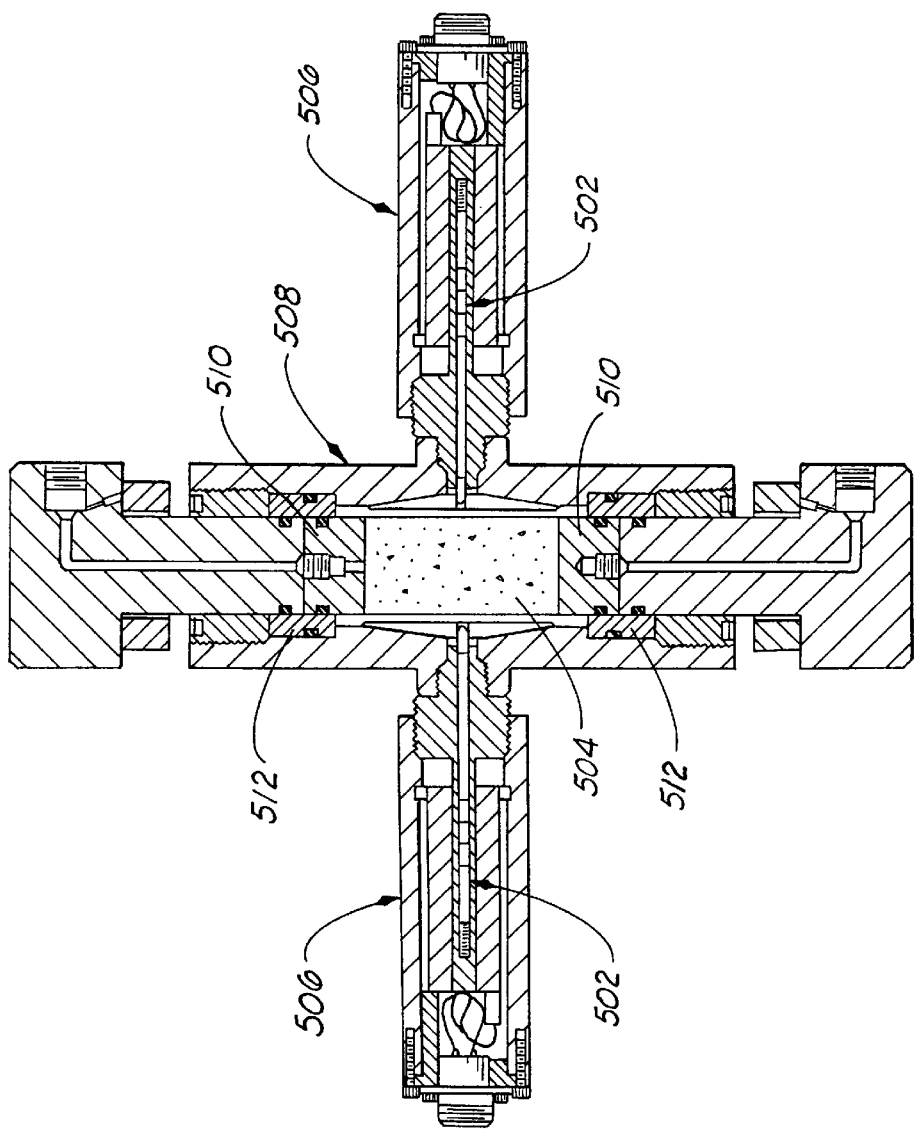
FIG. 3 is a sectional view of the prior art core sample test apparatus taken along line 3—3 in FIG. 1.

Although not shown in the embodiment of FIGS. 4 and 5, shorter end caps 46, 48 can be used to accommodate spacers as shown in FIGS. 2–3 depicting a prior art core sample test apparatus described above.

Connected to the end caps 46, 48 is a longitudinal (specifically, axial in the preferred embodiment) deflection sensing means for sensing a change in longitudinal dimension of the core sample 2 in response to an applied force. A support bracket 58 is connected by screws to the end cap 48, and a support bracket 62 is connected by screws to the end cap 46. Supported by the brackets 58, 62 and by rigid tubes 67 connected to the bracket 58 are two direct current linearly variable differential transducer assemblies 68 including respective calibration nuts 70, which are included in the longitudinal deflection sensing means of the illustrated embodiment. Additional sensors can be used in the same manner as desired. The assemblies 68 are of conventional type known in the art. Electrical connection with the assemblies is through electrical connectors 112 mounted on bracket 62.

In addition to the longitudinal deflection sensing means, there is lateral (specifically, radial in the preferred embodiment) deflection sensing means for sensing a change in lateral dimension of the core sample 2 in response to the applied force. In the preferred embodiment this includes four sensors 74 having respective probes communicating through the sealing sleeve 40 to detect lateral change in the core sample 2. Each of the sensors 74 includes a direct current linearly variable differential transducer assembly which can be of the same type as used for the longitudinal sensors. The transducer of the sensor 74 has a probe 78 in a pressure sealed housing that is held tightly against the sealing sleeve 40 by a compression spring 80 at the outer end of the probe 78. Each sensor 74 is retained in a respective comprising a rigid tube 200 threadedly connected to a rigid plug 202 having a threaded neck portion that screws into a respective one of the openings 24, 26 in the support body. An electrical connector 204 is connected at the opposite end of the rigid housing tube 200 to provide electrical communication with the internally contained sensor.

As shown in FIG. 4, the sensors 74 connected to the openings 24a, 26a are diametrically opposite each other, as are the sensors 74 connected to the openings 24b, 26b. Each of these pairs is at right angles to the other pair so that orthogonal measurements can be obtained to provide information about directional anisotropy in the specimen or to enable improved accuracy by averaging the diametrical changes. These sensors are coplanarly disposed due to the coplanar disposition of the openings 24a, 26a, 24b, 26b. These are also coplanar with the openings 24c, 26c.

Still referring to FIG. 4, the openings 24c, 26c are diametrically opposite each other along a line bisecting two of the right angles between the two sets of diametrically opposite sensors 74. The opening 24c is an access port through the outside of the housing 10 for an acoustic signal generating assembly positioned in direct contact with the sealing sleeve 40; although a specific acoustic signal generating assembly is not shown, it is generally represented by box 300. Also in FIG. 4, the opening 26c is an access port through the outside of the housing 10 for an acoustic signal receiver assembly in direct contact with the sleeve 40; this assembly is generally represented by box 302 in FIG. 4 (in FIG. 5, this port is simply closed by a plug 304). The acoustic signal generating assembly and the acoustic signal receiver assembly are conventional devices known in the art, such as ones which incorporate piezoelectric crystals for waveform (signal) creation and reception.

It is contemplated that other sensing and mounting devices and constructions can be used.

Mounted adjacent outer surface 22 of the support body 12 are heater bands (not shown).

The metallic components of the preferred embodiment housing and end caps depicted in the drawings are of any suitable material, such as stainless steel. The sealing elements are of any suitable material, such as an elastomer, that can be machined or preferably molded. All should be adapted for use in the high temperature, high pressure test environment preferably used.

The present invention also provides a method of determining elastic properties of a core sample taken from an oil or gas well. This will be described with reference to the preferred embodiment apparatus shown in the drawings.

The method comprises moving (preferably either pushing or dropping) the core sample 2 into the axial opening defined in the sealing member 40 of the test vessel that includes the housing 10 which supports the sealing member 40. The test vessel is closed by pushing the end members 46, 48 into the axial channel defined through the housing 10, wherein the stem of each end cap is adjacent the respective retaining member, washer and end of the sealing sleeve 40 as illustrated. The end members 46, 48 are movable relative to the housing 10 and the sealing member 40. The end caps 46, 48 are preferably slidable for easy insertion and extraction and for permitting movement in response to a longitudinal force applied by a press. When the end caps 46, 48 are installed as shown in the drawings, they support the core sample 2 at its two ends 4, 6.

To test the core sample 2 thus loaded in the housing 10 and sealing sleeve 40, pressure is applied and resultant dimensional changes are sensed by the sensors 68, 74. A compressive axial force can be applied to the core sample 2. This can be done by applying a force from a conventional press to the end members 46, 48 so that the end members 46, 48 move relatively closer to each other and thereby exert a force on the core sample 2 held therebetween in the sealing member 40. Furthermore, confining pressure can be applied radially toward the sealing member 40 by pumping a fluid through the opening 28 into the housing 10 around the outside of the sealing member 40. This simulates a well pressure and preferably can be up to at least about 10,000 psi.

Due to the symmetrical construction of the apparatus shown in the drawings, confining pressure is free to go from both ends of the core sample 2 to the center. Thus, the core sample 2 is free to give from both ends in response to the applied force(s). This keeps the greatest lateral or radial dimensional changes at the center of the core sample 2 where the transducers 74 are located, thereby ensuring reliable and consistent measurements from one core sample to another.

Pore pressure can also be applied to the core sample 2. This is done by pumping a fluid under pressure (up to but not exceeding the confining pressure) against at least one of the ends of the core sample 2. This pressure is applied through either or both of the ports 56 in the end members 46, 48.

The core sample 2 can be heated by electrically energizing the heating jackets. Heating preferably occurs until the temperature inside the sealing member 40 is at a temperature simulating a well temperature, such as up to 300° F.

With the desired conditions of the core sample 2 set, the resulting dimensional changes are sensed. This includes sensing the longitudinal or axial distance the core sample 2 is compressed as indicated by an electrical signal provided by the linearly variable differential transducers 68 in response to the movement between the two end members 46, 48 holding the core sample 2 in the sealing member 40. Calibration such as for deformation of the end caps 46, 48 can be made via the calibration nuts 70. A measurement of the distance or length of deformation can be determined from the transducer signals as known in the art.

Sensing dimensional changes also includes sensing the radial distance the core sample 2 is distended in response to the forces acting on the core sample. The radial deformation is sensed by measuring at four locations around the core sample, namely those locations where the linearly variable differential transducers probes are pressed in tight contact with the sealing sleeve 40 around the core sample 2. Electrical signals from the transducers 74 are used in known manner to provide measurements of the dimensional change. Calibration is made in known manner.

In the preferred embodiment, the aforementioned steps of sensing dimensional changes are performed concurrently. This is possible by using both the longitudinal and the lateral transducers in a single test apparatus as described.

Because the dimensional changes represent axial and radial strain of the cylindrical core sample 2 under the stress(es) applied by the exerted force(s), the preferred embodiment method of the present invention further comprises determining Young's modulus and Poisson's ratio. This is done in known manner in response to the applied stress and resultant measured strain.

Regarding acoustic testing, it involves the generation of an energy wave using an acoustic signal generating apparatus applied on one surface of the core sample specimen through the opening 24c and receiving the energy wave using an acoustic signal receiving apparatus applied on the opposite surface of the specimen through the opening 26c. The acoustic signal generating apparatus and the acoustic receiving apparatus are conventional devices known in the art. This acoustic testing occurs concurrently with the aforementioned static test wherein one or more parameters of the core sample are measured in the test vessel under the applied pressure. For example, strain of the core sample is measured as described above at various pressures (e.g., 1,000 pounds per square inch, 2,000 pounds per square inch, etc.), and the acoustic information is determined at these same test pressures.

The information recorded during this acoustic testing is the elapsed time between signal generation and signal reception on opposing sides of the specimen. These times are generally in the range of tens of microseconds. Additionally, the sample dimensions must be accurately known to allow calculation of the travel speed of the signal in the material.

The travel speeds of various types of waveforms (e.g., compressional waves and shear waves) known in the industry are used in corresponding equations in the industry to calculate dynamically determined mechanical property values of the specimen material. Incorporation of acoustic travel time determination concurrently with the performance of strain measurement provides for an evaluation of the impact of stress magnitude on the variation of dynamically determined mechanical property values. That is, a correlation between the acoustic travel time derived dynamic mechanical properties and the strain derived static properties can be determined. Heretofore dynamic mechanical property values have been obtained using acoustic logs obtained from logging the actual well. Different correlation factors have been used to try to correlate these values with static property values, but the present invention now provides an easy to use laboratory tool in which both types of properties can be determined from concurrently made measurements and actual correlations computed from the laboratory test data.

Once the core sample 2 has been tested and the pressure and temperature returned to ambient conditions, the core sample 2 can be easily removed so that another core sample can be tested by repeating the foregoing steps if desired. The core sample 2 is removed from the sealing member 40 without removing the sealing member 40 from the housing 10. This is done by removing one or both of the end members 46, 48 from the test vessel and quickly and easily sliding the core sample 2 out without removing the sealing member 40. Another core sample can then be quickly loaded in by sliding or dropping it into the retained sealing sleeve 40. Therefore, the present invention is reusable without requiring replacement or manipulation of the sealing sleeve 40 (unless, for example, it has been damaged).

Thus, the present invention is well adapted to carry out the objects and attain the ends and advantages mentioned above as well as those inherent therein. While preferred embodiments of the invention have been described for the purpose of this disclosure, changes in the construction and arrangement of parts and the performance of steps can be made by those skilled in the art, which changes are encompassed within the spirit of this invention as defined by the appended claims.

What is claimed is:

1. An apparatus for testing a core sample extracted from an oil or gas well, comprising:
    a housing having first and second ends;
    a sealing sleeve fixed inside said housing and adapted to receive a core sample without said sealing sleeve being removed from said housing;
    a first retainer, disposed within the first end of said housing;
    a second retainer, disposed within the second end of said housing;
    a first longitudinal deflection sensor connected to said first and second retainers;
    a second longitudinal deflection sensor connected to said first and second retainers;
    a first lateral deflection sensor;
    a first pressure sealed container connected to said housing, said first pressure sealed container having said first lateral deflection sensor disposed therein;
    a second lateral deflection sensor;
    a second pressure sealed container connected to said housing, said second pressure sealed container having said second lateral deflection sensor disposed therein;
    a third lateral deflection sensor;
    a third pressure sealed container connected to said housing, said third pressure sealed container having said third lateral deflection sensor disposed therein;
    a fourth lateral deflection sensor; and
    a fourth pressure sealed container connected to said housing, said fourth pressure sealed container having said fourth lateral deflection sensor disposed therein;
    wherein said housing has an acoustic signal generator access port and an acoustic signal receiver access port defined therein; and
    wherein:
        said first and second lateral deflection sensors are connected to said housing by said first and second pressure sealed containers diametrically opposite each other;
        said third and fourth lateral deflection sensors are connected to said housing by said third and fourth pressure sealed containers diametrically opposite each other and at right angles to said first and second lateral deflection sensors; and
        said acoustic signal generator access port and said acoustic signal receiver access port are diametrically opposite each other along a line bisecting two of the right angles between said first and second lateral deflection sensors and said third and fourth lateral deflection sensors.

2. An apparatus as defined in claim 1, wherein said first, second, third and fourth lateral deflection sensors, said acoustic signal generator access port and said acoustic signal receiver access port are coplanar.

3. An apparatus for testing a core sample extracted from an oil or gas well, comprising:
    a housing having first and second ends;
    a sealing sleeve fixed inside said housing and adapted to receive a core sample without said sealing sleeve being removed from said housing;
    a first retainer, disposed within the first end of said housing;
    a second retainer, disposed within the second end of said housing;
    a first longitudinal deflection sensor connected to said first and second retainers;
    a second longitudinal deflection sensor connected to said first and second retainers;

a first lateral deflection sensor;

a first pressure sealed container connected to said housing, said first pressure sealed container having said first lateral deflection sensor disposed therein;

a second lateral deflection sensor;

a second pressure sealed container connected to said housing, said second pressure sealed container having said second lateral deflection sensor disposed therein;

a third lateral deflection sensor;

a third pressure sealed container connected to said housing, said third pressure sealed container having said third lateral deflection sensor disposed therein;

a fourth lateral deflection sensor; and a fourth pressure sealed container connected to said housing, said fourth pressure sealed container having said fourth lateral deflection sensor disposed therein;

wherein:
  said first and second lateral deflection sensors are connected to said housing by said first and second pressure sealed containers diametrically opposite each other; and
  said third and fourth lateral deflection sensors are connected to said housing by said third and fourth pressure sealed containers diametrically opposite each other and at right angles to said first and second lateral deflection sensors.

4. An apparatus as defined in claim 3, wherein said first, second, third and fourth lateral deflection sensors are coplanar.

5. An apparatus for testing a core sample extracted from an oil or gas well, comprising:

a housing having first and second ends;

a sealing sleeve fixed inside said housing and adapted to receive a core sample without said sealing sleeve being removed from said housing;

a first retainer, disposed within the first end of said housing;

a second retainer, disposed within the second end of said housing;

a first longitudinal deflection sensor connected to said first and second retainers;

a second longitudinal deflection sensor connected to said first and second retainers;

a first lateral deflection sensor;

a first pressure sealed container connected to said housing, said first pressure sealed container having said first lateral deflection sensor disposed therein;

a second lateral deflection sensor;

a second Pressure sealed container connected to said housing, said second pressure sealed container having said second lateral deflection sensor disposed therein;

a third lateral deflection sensor;

a third pressure sealed container connected to said housing, said third pressure sealed container having said third lateral deflection sensor disposed therein;

a fourth lateral deflection sensor; and a fourth pressure sealed container connected to said housing, said fourth pressure sealed container having said fourth lateral deflection sensor disposed therein;

wherein said housing includes:
  a support body having an inner surface providing support for said sealing sleeve inside said body;
  a first washer disposed within said support body adjacent an end of said sealing sleeve such that said first washer is not rotatable relative to said support body and said sealing sleeve fixed to said body; and
  a second washer disposed within said support body adjacent another end of said sealing sleeve such that said second washer is not rotatable relative to said support body and said sealing sleeve fixed to said body.

6. An apparatus for testing a core sample extracted from an oil or gas well, comprising:

a housing having first and second ends;

a sealing sleeve fixed inside said housing and adapted to receive a core sample without said sealing sleeve being removed from said housing;

a first retainer, disposed within the first end of said housing;

second retainer, disposed within the second end of said housing;

longitudinal deflection sensing means for sensing a change in longitudinal dimension of the core sample in response to an applied force;

lateral deflection sensing means for sensing a change in lateral dimension of the core sample in response to the applied force; and wherein said housing includes:
  a support body having an inner surface providing support for said sealing sleeve inside said body;
  a first washer disposed within said support body adjacent an end of said sealing sleeve such that said first washer is not rotatable relative to said support body and said sealing sleeve fixed to said body; and
  a second washer disposed within said support body adjacent another end of said sealing sleeve such that said second washer is not rotatable relative to said support body and said sealing sleeve fixed to said body.

7. An apparatus as defined in claim 6, wherein:

said support body has a first channel defined in the inner surface thereof at the first end of said housing;

said support body has a second channel defined in the inner surface thereof at the second end of said housing;

said first washer has a first key extending into said first channel; and said second washer has a second key extending into said second channel.

8. An apparatus for testing a core sample extracted from an oil or gas well, comprising:

a housing having first and second ends;

a sealing sleeve fixed inside said housing and adapted to receive a core sample without said sealing sleeve being removed from said housing;

a first retainer, disposed within the first end of said housing;

a second retainer, disposed within the second end of said housing; and said housing further having an acoustic signal generator access port and an acoustic signal receiver access port defined through the outside of said housing.

9. An apparatus as defined in claim 8, further comprising:

longitudinal deflection sensing means for sensing a change in longitudinal dimension of the core sample in response to an applied force; and lateral deflection sensing means for sensing a change in lateral dimension of the core sample in response to the applied force.

10. An apparatus as defined in claim 9, wherein said acoustic signal generator access port and said acoustic signal receiver access port are diametrically opposite each other.

11. An apparatus as defined in claim 10, wherein said acoustic signal generator access port and said acoustic signal receiver access port are coplanar.

12. An apparatus as defined in claim 7, wherein said acoustic signal generator access port and said acoustic signal receiver access port are diametrically opposite each other.

13. An apparatus as defined in claim 12, wherein said acoustic signal generator access port and said acoustic signal receiver access port are coplanar.

14. An apparatus as defined in claim 8, wherein said housing further includes:
   a support body having an inner surface providing support for said sealing sleeve inside said body;
   a first washer disposed within said support body adjacent an end of said sealing sleeve such that said first washer is not rotatable relative to said support body and said sealing sleeve fixed to said body; and
   a second washer disposed within said support body adjacent another end of said sealing sleeve such that said second washer is not rotatable relative to said support body and said sealing sleeve fixed to said body.

15. An apparatus as defined in claim 14, wherein:
   said support body has a first channel defined in the inner surface thereof at the first end of said housing;
   said support body has a second channel defined in the inner surface thereof at the second end of said housing;
   said first washer has a first key extending into said first channel; and
   said second washer has a second key extending into said second channel.

16. A method of testing a core sample extracted from an oil or gas well, comprising steps of:
   (a) applying pressure to a core sample in a test vessel;
   (b) measuring a parameter of the core sample in the test vessel resulting from the applied pressure; and
   (c) concurrently with steps (a) and (b), performing an acoustic test on the core sample in the test vessel.

17. A method as defined in claim 16, wherein step (b) includes measuring strain of the core sample and step (c) includes propagating an acoustic signal across the core sample in the test vessel and measuring a propagation time therefor.

18. A method as defined in claim 16, further comprising correlating the acoustic test of step (c) with the measured parameter of step (b).

19. A method as defined in claim 16, further comprising:
   repeating steps (a), (b) and (c) to obtain a plurality of sets of pressure applications, parameter measurements and acoustic test measurements; and
   correlating the acoustic test measurement of each of the sets with the parameter measurement of the same set.

* * * * *